United States Patent [19]

Taylor

[11] Patent Number: 4,763,512

[45] Date of Patent: Aug. 16, 1988

[54] RHEOMETER

[76] Inventor: James C. Taylor, Gregge Street, Heywood, Lancashire, England, OL10 2ED

[21] Appl. No.: 923,317

[22] Filed: Oct. 14, 1986

[30] Foreign Application Priority Data

Oct. 14, 1985 [GB] United Kingdom ............... 8525255

[51] Int. Cl.⁴ .......................................... G01N 11/00
[52] U.S. Cl. ...................................................... 73/54
[58] Field of Search ...................................... 73/54, 57

[56] References Cited

U.S. PATENT DOCUMENTS 3,745,811 7/1973 Dure et al. ............................. 73/54
4,602,501 7/1986 Hirata .................................... 73/54

Primary Examiner—Stewart J. Levy
Assistant Examiner—Hezron E. Williams
Attorney, Agent, or Firm—Wenderoth, Lind & Ponack

[57] ABSTRACT

A rheometer for measuring viscoelasticity with a complex rigidity function comprises a tube for holding the fluid, means for oscillating the tube in the direction of its axis, detector means for detecting the position of the sample of fluid, and an analyzer for relating the movement of the fluid sample to the movement of the drive to derive viscosity characteristics.

4 Claims, 1 Drawing Sheet

RHEOMETER

The invention relates to a rheometer for measuring the viscous characteristics of a fluid using an oscillating capillary technique.

BACKGROUND OF THE INVENTION

Many fluids are not rheologically simple, that is to say they have properties which cannot be described by a single figure for viscosity. The present invention is particularly applicable to the measurement of viscosity of this class of materials.

Materials which possess viscoelasticity can be described by the complex rigidity function $$G^* = G' + j\,G''$$

where G' and G'' represent the parts of the complex rigidity modulus which are respectively in phase and in quadrature with the applied stress. Both G' and G'' are functions of frequency.

OBJECT AND BRIEF SUMMARY OF THE INVENTION

The present invention seeks to provide a rheometer capable of evaluating G' and G'' (or equivalent properties) over a range of frequencies.

According to the invention there is provided a rheometer comprising a tube for holding a sample of a fluid to be investigated, the tube having an axis; drive means for imparting oscillatory movement to the tube in the direction of its axis; means for adjusting the frequency of the drive means; detector means for detecting the position of the sample during the oscillatory movement; and an analyzer for receiving inputs from the detector means and from the drive means to relate the movement of the sample to the amplitude and frequency of the movement of the tube and thereby derive viscosity characteristics for the fluid over a frequency range.

The axis of the tube in one embodiment of the invention is straight, and the drive means comprises a linear actuator. In another embodiment the axis of the tube is a circular arc and the drive means is a rotator which oscillates the tube about the centre of the circle.

The drive means is programmed to effect oscillations with predetermined amplitude and frequency and preferably there is a position transducer associated with the tube to provide feedback signals for the drive control.

The detector for the position of the fluid sample may take one of several forms. Firstly it may either measure the position of the sample relative to the bed of the rheometer or relative to the tube. The analyzer, which preferably embodies a computer, will be arranged to determine the relationship of the absolute movement of the fluid as a response to the absolute movement of the tube. Secondly, the type of the detector may be optical, including laser ranging, physical with movable contact probes, or electrical using capacitive effects, for example.

BRIEF DESCRIPTION OF THE DRAWINGS

The invention will further be described with reference to the accompanying drawing, of which.

DETAILED DESCRIPTION OF THE INVENTION

Figure 1:
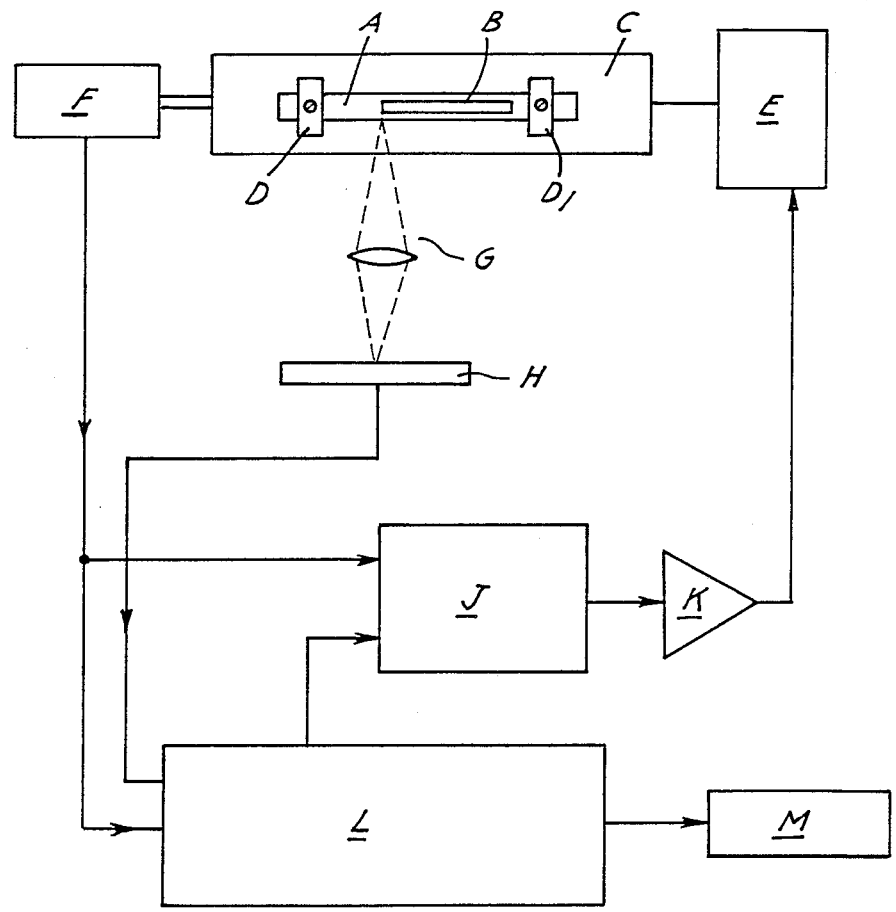
FIG. 1 is a block schematic diagram of a rheometer in accordance with the invention.

Referring to the drawing, the rheometer comprises a transparent tube A containing a quantity of fluid B (the properties of which are to be evaluated), carried on a plate C, whereon it is secured by clamps D. The tube A is vented to atmosphere at both ends. Alternatively, the tube may be sealed provided that there is a cushion of air or other gas at each end so that the fluid may move. A force-generating transducer E, typically a moving coil in a magnetic field, is fastened to the plate C so as to be able to move it translationally along the axis of the tube A. A second transducer F, typically an LVDT or capacitor system, is also fastened to the plate C so as to be able to measure the actual motion of the plate and hence of tube A.

An optical system G is used to image one end of the fluid B onto an optical sensor H, so as to be able to sense the motion of the fluid relative to the (presumed immovable) frame of the instrument.

Force transducer E is fed with an alternating current generated by an oscillator J and amplified by a linear amplifier K. Feedback is used from transducer F so that the actual amplitude of movement of the tube may be measured and controlled.

The optical transducer H, sensing the longitudinal movement of the fluid, feeds into a computer system L where computations are made of the relative phase and amplitude of the motions of the tube and of the fluid. From these measurements of relative phase and amplitude, it is possible to compute the properties of the material. A numerical read-out is given by a display M.

In practice, the system will be driven at a series of frequencies selected in a step fashion, for a period sufficiently long for all transient phenomena to cease. Measurements will then be made over several cycles of oscillation to allow improved accuracy to be obtained.

If desired, the values obtained for G' and G'' at each frequency may be fitted to an equation so as to characterise the material in the best manner possible.

Figure 2:
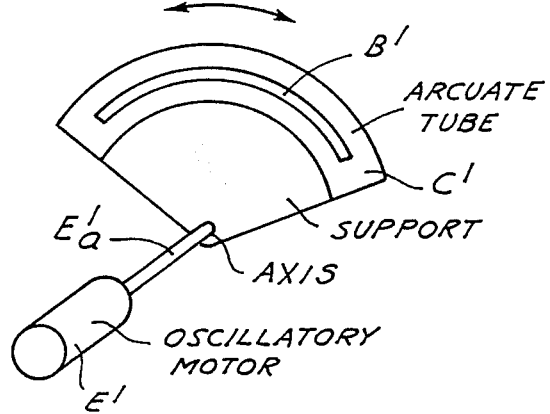
FIG. 2 is a schematic perspective view of a part of a second embodiment of the invention.

Alternatively, as shown in FIG. 2, the tube A' can be along a circular arc, and the plate C' can be oscillated by an oscillatory motor E' around the axis of rotation of the motor shaft E'a which lies on the center of the circle. The remainder of the elements of the apparatus are the same as for the embodiment of FIG. 1.

The invention is not restricted to the details of the embodiment described above with reference to the drawings. For example, the tube may be opaque, and probes may be inserted along the axis of the tube. These probes may then be advanced slowly until they touch the oscillating fluid at the peak of the motion. From this may be derived once again the relative amplitude and phase of the motion. The force transducer may take the form of a moving iron piece in a magntic field modulated by means of an electric current. Alternatively, it may take the form of a motor driving a cam or eccentric.

The optical sensor may comprise an array of light-sensitive devices or a television camera tube. The sensor may take other forms, for example a physical probe may be advanced along the tube axis until it touces the fluid. A laser beam may be used for range-finding the sample of fluid. The motion of the fluid may be sensed by means of the radiation scattered side-ways through the tube. A capacitive sensor arrangement may be used.

What I claim is:

1. A rheometer comprising a tube for holding a sample of a fluid to be investigated, the tube having an axis; drive means for imparting oscillatory movement to the tube in the direction of its axis; means for adjusting the frequency of the drive means over a frequency range; detector means for detecting the position of the sample during the oscillatory movement; and an analyzer for receiving inputs from the detector means and from the drive means to relate the movement of the sample to the amplitude and frequency of the movement of the tube and thereby derive viscosity characteristics for the fluid over said frequency range.

2. A rheometer as claimed in claim 1 wherein the axis of the tube is straight and the drive means comprises a linear actuator.

3. A rheometer as claimed in claim 1 wherein the axis of the tube is a circular arc and the drive means is a rotator which oscillates the tube about the centre of the circle.

4. A rheometer as claimed in any of the preceding claims wherein the drive means is programmed to effect oscillations with predetermined amplitude and frequency and there is provided a position transducer associated with the tube to provide feedback signals for the drive control.

* * * * *